United States Patent [19]

Pittrof et al.

[11] Patent Number: 5,376,646
[45] Date of Patent: Dec. 27, 1994

[54] TOPICAL PREPARATIONS CONTAINING THE SALT OF A CHOLANIC ACID AND A LIPID

[75] Inventors: Folker Pittrof, Freiburg, Germany; Andreas Supersaxo, Cupertino, Calif.

[73] Assignee: Hoffmann-La Roche Inc., Nutley, N.J.

[21] Appl. No.: 77,811

[22] Filed: Jun. 16, 1993

Related U.S. Application Data

[63] Continuation of Ser. No. 642,618, Jan. 17, 1991, abandoned.

[30] Foreign Application Priority Data

Jan. 24, 1990 [CH] Switzerland ............... 222/90

[51] Int. Cl.$^5$ ............ A61K 31/685; A61K 31/56; A61K 31/535; A61K 31/20; A61K 31/16
[52] U.S. Cl. ............ 514/78; 514/171; 514/182; 514/239.5; 514/559; 514/629; 514/947
[58] Field of Search ............ 514/78, 171, 182, 239.5, 514/559, 629, 947

[56] References Cited

U.S. PATENT DOCUMENTS

| | | | |
|---|---|---|---|
| 3,873,700 | 3/1975 | Misato et al. | 424/199 |
| 4,115,313 | 9/1978 | Lyon et al. | 252/309 |
| 4,156,719 | 5/1979 | Sezaki et al. | 424/118 |
| 4,158,707 | 6/1979 | Steffen et al. | 424/244 |
| 4,396,612 | 8/1983 | Candussi et al. | 424/180 |
| 4,626,529 | 12/1986 | Grollier | 514/159 |
| 4,681,876 | 7/1987 | Marples et al. | 514/182 |
| 4,694,084 | 9/1987 | Breuninger et al. | 546/25 |
| 4,826,871 | 5/1989 | Gressel et al. | 514/438 |
| 4,857,514 | 8/1989 | Lippa et al. | 514/78 |
| 4,882,164 | 11/1989 | Ferro et al. | 424/450 |
| 5,034,228 | 7/1991 | Meybeck et al. | 424/401 |
| 5,179,079 | 1/1993 | Hansen et al. | 514/4 |

FOREIGN PATENT DOCUMENTS

| | | |
|---|---|---|
| 154977 | 3/1985 | European Pat. Off. . |
| 388817 | 3/1990 | European Pat. Off. . |

OTHER PUBLICATIONS

Derwent Abstract No. 85–231681/38 of EPA 154 977. (1985).
Derwent Abstract No. 90–291784/39 of EPA 388 817. (1990).
Derwent Abstract No. 87–200045/29 for U.S. Pat. No. 5,034,228 (1987).
Dorland's Medical Dictionary, 26th Edition, (one page). (1991).
Eiermann, Heinz J., Cosmetic Labeling Issues–And Answers, Cosmetics & Toiletries, vol. 103, Jul. 1988.

*Primary Examiner*—Marianne M. Cintins
*Assistant Examiner*—Kimberly R. Jordan
*Attorney, Agent, or Firm*—George M. Gould; George W. Johnston; John P. Parise

[57] ABSTRACT

Topical preparations containing a salt of a cholanic acid, a lipid, and optionally, one or more other pharmaceutically or cosmetically active substances, are disclosed. These preparations are used in pharmaceutical and/or cosmetic applications.

5 Claims, No Drawings

TOPICAL PREPARATIONS CONTAINING THE SALT OF A CHOLANIC ACID AND A LIPID

This is a continuation of application Ser. No. 07/642,618, filed Jan. 17, 1991, now abandoned.

The present invention relates to topical preparations which contain a salt of a cholanic acid, a lipid and, optionally, one or more other pharmaceutically or cosmetically active substances. These preparations are useful in pharmaceutical and/or cosmetic applications.

The preparations of the present invention have advantageous properties over conventional formulations including the improved penetration of the active substance and its improved distribution in the skin. This is true not only for hydrophilic active substances, but also for lipophilic active substances. In the case of lipophilic active substances, there is the additional advantage that organic solvents which typically have a poor compatibility, are not necessary. In addition, the preparations of the invention are preferable to conventional liposomal formulations inasmuch as they have improved physical stability and are generally cheaper to manufacture.

DETAILED DESCRIPTION OF THE INVENTION

Cholanic acid salts useful in the present preparations include the salts of cholanic acids or cholanic acid derivatives which are described in U.S. Pat. No. 4,158,707 (counterpart to DE-OS 2 730 570), which is hereby incorporated by reference. Particularly preferred cholanic acid salts are cholates, glycocholates, deoxy-cholates and taurocholates, especially the alkali salts, such as the sodium salts. Sodium glycocholate is especially preferred.

Useful lipids in the present preparations include phosphatidylcholines, for example natural lecithins or synthetic lecithins having modified side-chains, for example those which are described in U.S. Pat. No. 4,694,084 (counterpart to European Patent Application A2-0154977), which is hereby incorporated by reference. Natural lecithins such as egg lecithin or soya lecithin are preferred.

In the present novel preparations, the molar ratio of lipid to cholanic acid salt is from about 0.1:1 to about 2:1. Ratios of from about 0.1:1 to about 1.5:1 are preferred.

The active substances or ingredients which may be incorporated in the preparations in accordance with the invention include all therapeutically and cosmetically active substances which are suitable for application to skin and mucous membranes, including the eyes. Examples of such active substances include the corticosteroids such as hydrocortisone, hydrocortisone acetate, prednisolone, fluorocortolone, triamcinolone acetate; sex hormones such as estriol, estradiol, estradiol benzoate; antiphlogistics such as indomethacin, bufexamac, salicylic acid, salicylamide; immunosuppressives such as cyclosporin A, FK 506 and immunosuppressive retinoids such as (all-E)-3,7-dimethyl-9-(2-trifluoromethyl)-6-nonyloxyphenyl-2,4,6,8-nonatetraenoic acid; antibiotics such as neomycin, gentamycin, polymyxin B, bacitracin, gramidicin, tyrothricin, erythromycin, clindamycin, tetracyclins, chloramphenicol, fusidic acid, nitrofural; antimycotics such as tolnaftate, imidazole derivatives (e.g. miconazole, econazole), amorolfin, nystatin, amphotericin B, flucytosine, griseofulvin; virustatics and cytostatics such as idoxuridine, tromantadine, acylovir, podophyllin, 5-fluorouracil; antipsoriatics such as anthralin and psoralens; retinoids such as tretinoin, isotretinoin, arotinoids; sunscreen agents such as p-aminobenzoic acid derivatives, benzimidazole derivatives, cinnamic acid derivatives; skin care agents such as panthenol; vitamins such as tocopherol; moisturizing agents such as pyrrolidonecarboxylic acids and their Na salts, lactic acid and its Na salts, perfusion-promoting agents such as nicotinic acid derivatives and capsicides. Further examples of active substances are heparin, PAF antagonists, leukotriene antagonists, antihistamines, mast cell blockers, local anaesthetics, peptides and proteins, especially cytokines, for example interferon and interleukin.

Solutions, lotions, sprays, creams, gels, salves and foams are examples of topical application forms. For example the preparations may be in the form of an aqueous solution of cholanic acid salt-lipid-mixed micelles.

The preparations of the invention are manufactured using conventional methods and technology known to those skilled in the art.

Gels are obtained from solutions of the above-described preparations by adding one or more conventional anionic (e.g. carbomer, carboxymethylcelluloses and their salts, xanthanes, bentonite, montmorillonite), cationic (e.g. polyquaternium) or non-ionic gel formers. Preferably, non-ionic gel formers are used. Preferred non-ionic gel formers include: methylcellulose, hydroxyethylcellulose, hydroxypropylcellulose, hydroxy- propylmethylcellulose, polyvinylpyrrolidone, polyvinyl alcohols and their copolymers, for example with vinyl acetate copolymers.

Foams can be present as ethanol-containing aqueous mixed micelle solutions in pressurized containers, which contain about 10 wt. % of a propellant, such as FKW 12/114 (40:60). Alternatively, foams can be produced by spraying from pressurized containers. Sprays can be produced from the above solutions using a conventional spray nozzle.

For the preparation of creams and salves, an aqueous micellar active substance solution is prepared, for example as described in U.S. Pat. No. 4,158,707 (which has been incorporated by reference). This solution is incorporated in a conventional cream or salve base. Any conventional cream or salve base is suitable for this purpose. Such bases can be prepared from known adjuvants such as polyethylene glycols, paraffins, waxes, fats and fat-like substances and can be present as an oil-in-water or as a water-in-oil type.

The preparations in accordance with this invention can contain adjuvants and additives, including penetration-enhancers such as unsaturated fatty acids, e.g. oleic acid. The preparations may include conventional preservatives (for example p-hydroxybenzoic acid esters, benzyl alcohol, phenoxy-ethanol, chlorhexidine salts); antioxidants (for example BHT, BHA, tocopherol, ascorbic acid); complexing agents (for example $Na_2EDTA$); buffers (for example citric acid, phosphoric acid); moisturizing agents (for example propylene glycol, glycerol, sugars and sugar alcohols, e.g. sorbitol); as well as water and other solvents such as ethanol, DMSO or organic amides.

The preparations in accordance with the invention can be applied to the skin, to mucous membranes, e.g. buccally or nasally as a gel, solution, chewable capsule or buccal tablet; to the eyes as a cream, salve, gel or solution; and to the respiratory tract as a spray.

Mixed micelle solutions of pharmaceutically active substances can also be used in transdermal application systems. Thus, the invention also embraces transdermal preparations in which the combination of active substance, cholanic acid (salt) and lipid is present as a solution or in dried, e.g. in lyophilized, form.

The preparations of the present invention are well tolerated by the skin, the mucous membranes and the eyes.

Primary eye and skin irritation tests with mixed micelle formulations containing a salt of a cholanic acid and a lipid were carried out in accordance with the OECD guidelines. These preparations in accordance with the present invention were all found to be "non-irritating" in comparison to conventional solubilizates (e.g. with sodium lauryl sulphate).

It has been found that topical formulations according to the present invention which do not contain an active substance in addition to the cholanic acid salt and lipid mixed have an antimycotic activity. The invention thus also includes preparations for topical administration which do not contain pharmaceutically active substances in addition to a cholanic acid salt and a lipid.

EXAMPLES

The invention is illustrated further by the following Examples.

In the Examples, all operations were carried out under an inert gas; the solvents were freed from oxygen by the introduction of inert gas.

EXAMPLE 1

1.75 g of glycocholic acid, 1.50 g of soya lecithin, 0.278 g of amorolfin HCl and 1.0 g of benzyl alcohol were dissolved until clear in 10.0 g of ethanol (or another suitable organic solvent) at about 45°–50° C. (solution A). Next, 3.75 ml of a 1N NaOH solution were added to 80 ml of deionized water. This solution was added to solution A while stirring and the mixture was made up to 100.0 g with water.

EXAMPLE 2

1.75 g of glycocholic acid were suspended in about 50 g of deionized water and dissolved by adding NaOH. After adjusting to a pH value of 6.0, 1.50 g of soya lecithin, 0.278 g of amorolfin HCl and 1.0 g of benzyl alcohol were dissolved in succession (solution A). The dissolution operation can be accelerated by ultrasonics and/or warming. Next, 1.60 g of methylcellulose 4000 cP were suspended in 5.0 g of propylene glycol and added to solution A while stirring. The mixture was made up to 100.0 g with water and the gel was stirred slowly at 5° C. until the methylcellulose was completely swollen.

EXAMPLE 3

Gels for the topical administration of amorolfin having the following compositions were manufactured in the same manner set forth in Examples 1 and 2 above:

|  | 3a | 3b | 3c |
| --- | --- | --- | --- |
| Amorolfin HCl | 0.278 | 0.278 | 0.278 g |
| Benzyl alcohol | 1.00 | 1.00 | 1.00 g |
| Propylene glycol | 5.00 | 5.00 | 5.00 g |
| Lecithin | 1.50 | 1.5 | 7.45 g |
| Glycocholic acid | 1.75 | 1.75 | 5.38 g |
| NaOH ad pH 6.0–6.2 | q.s. | q.s. | q.s. |
| Methylcellulose | 1.6 | — | — g |
| Hydroxyethylcellulose | — | 1.80 | 1.80 g |
| Ethanol | — | 10.0 | — g |
| Water ad | 100.0 | 100.0 | 100.0 g |

The penetration data presented in Table I below show that with the cholanic acid salt/lecithin systems of the present invention, much higher active substance concentrations can be achieved not only in the cornea but also in the lower layers of the skin in comparison to administration using conventional creams.

TABLE I

| Formulation | Dosage | Time (h) | Skin surface | Str. corneum | Remaining skin | Chamber fluid |
| --- | --- | --- | --- | --- | --- | --- |
| Gel of Ex. 3a | 0.25% | 16 | 9.99 66.6 | 1.74 11.6 | 3.22 21.5 | 0.05 ($\mu$g/cm$^2$) 0.3 (%) |
| Gel of Ex. 3b | 0.25% | 16 | 5.04 33.6 | 3.71 24.7 | 6.21 41.4 | 0.04 ($\mu$g/cm$^2$) 0.3 (%) |
| Gel of Ex. 3c | 0.25% | 16 | 11.92 79.4 | 1.41 9.4 | 1.65 11.0 | 0.02 ($\mu$g/cm$^2$) 0.1 (%) |
| Cream | 0.25% | 16 | 14.19 94.6 | 0.32 2.1 | 0.48 3.2 | 0.01 ($\mu$g/cm$^2$) 0.1 (%) |

EXAMPLE 4

A mixed micelle solution of isotretinoin having the following composition was prepared according to the procedures set forth in Example 1 above:

| Isotretinoin | 50 mg |
| --- | --- |
| dl-$\alpha$-Tocopherol | 10 mg |
| Na$_2$ EDTA | 30 mg |
| Lecithin | 16.9 g |
| Glycocholic acid | 8.85 g |
| Benzyl alcohol | 1.0 g |
| NaOH ad pH 6 | q.s. |
| Water ad | 100.0 g |

This mixed micelle solution can be processed to a gel according to the procedure set forth in Example 2 above. The gel can be used for topical treatment e.g. of acne.

EXAMPLE 5

A mixed micelle solution of tretinoin having the following composition was prepared as described above:

| Tretinoin | 20 mg |
| --- | --- |
| dl-$\alpha$-Tocopherol | 10.0 mg |
| Lecithin | 16.9 g |
| Glycocholic acid | 8.85 g |
| NaOH ad pH 6 | q.s. |
| Benzyl alcohol | 1.0 g |
| Water ad | 100.0 ml |

This mixed micelle solution can be processed to a gel as described in Example 2. The gel can also be used for topical treatment, e.g. of acne.

EXAMPLE 6

A mixed micelle solution for topical use in psoriasis having the following composition was prepared as described above:

| Methyl p-[2-(5,6,7,8-tetrahydro- | 0.05 g |
| --- | --- |

-continued

| | |
|---|---|
| 5,5,8,8-tetramethyl-2-naphthyl)-propyl]phenylsulphone | |
| Lecithin | 16.90 g |
| Glycocholic acid | 8.85 g |
| NaOH ad pH 6.0 | q.s. |
| Benzyl alcohol | 1.00 g |
| Water ad | 100.00 g |

The solution can be converted into a gel as described in Example 2.

EXAMPLE 7

Mixed micelle solutions for the manufacture of a hydrocortisone spray having following composition were prepared according to the procedures of Wholrab and Lasch, Dermatologica 174:18 (1987):

| | (a) | (b) |
|---|---|---|
| Hydrocortisone | 0.25 | 0.50 g |
| Lecithin | 8.00 | 10.58 g |
| Glycocholic acid | 5.00 | 8.06 g |
| NaOH ad pH 6.0 | q.s. | q.s. |
| Benzyl alcohol | 1.00 | 1.00 g |
| Water ad | 100.00 | 100.00 g |

As evidenced by the data in Table II below, an improved tissue level of hydrocortisone in the skin was achieved with the mixed micelle solutions of the present invention in comparision to conventional liposomal carriers.

TABLE II

| Formulation | Dosage | Time (h) | Skin surface | Str. corneum | Remaining skin | Chamber fluid |
|---|---|---|---|---|---|---|
| Mixed micellee solution (a) of Ex. 7 | 0.25% | 6 | 12.39 82.6 | 1.48 9.9 | 1.04 6.9 | 0.09 ($\mu$g/cm$^2$) 0.6 (%) |
| Liposome sol. | 0.25% | 6 | 13.46 89.7 | 0.68 4.5 | 0.84 5.6 | 0.02 ($\mu$g/cm$^2$) 0.1 (%) |

Solutions 7a and 7b can be used as sprays for topical application, for example for the therapy of inflammatory skin disorders.

EXAMPLE 8

A mixed micelle solution of panthenol having the following composition was prepared as described above:

| | |
|---|---|
| D-Panthenol | 0.50 g |
| Lecithin | 8.00 g |
| Glycocholic acid | 5.00 g |
| NaOH ad pH 6.0 | q.s. |
| Benzyl alcohol | 1.00 g |
| Water ad | 100.00 g |

The solution can be used as a spray for the treatment of damaged skin.

As is shown in Table III below, significantly higher panthenol concentrations in the skin were achieved with the preparation of Example 8 according to the present invention than with a conventional salve.

TABLE III

| Formulation | Panthenol content | Time (h) | Skin surface | Str. corneum | Remaining skin | Chamber fluid |
|---|---|---|---|---|---|---|
| Solution of Ex. 8 | 0.50% | 6 | 222.6 74.2 | 51.99 17.3 | 22.44 7.5 | 2.9 ($\mu$g/cm$^2$) 1.9 (%) |
| Conventional salve | 0.50% | 6 | 300.9 96.4 | 7.70 2.5 | 2.98 1.0 | 0.43 ($\mu$g/cm$^2$) 0.1 (%) |

EXAMPLE 9

A cyclosporin A mixed micelle solution having the following composition was prepared as described below:

| | |
|---|---|
| Cyclosporin A | 1.7–3.7 mg |
| Lecithin | 30.8–92.4 mg |
| Na glycocholate | 19.5–58.5 mg |
| Water or buffer ad | 1.0 ml |

Lecithin (Lipoid E PG, Lipoid KG), sodium glycocholate and cyclosporin were dissolved in 5 ml of chloroform/methanol (1:1, v/v) in a round flask. The film which resulted after evaporation of the organic solvent (40° C.) was dispersed in 1 ml of water and adjusted to pH 6.0±0.1 with 1N HCl. Buffer solutions, such as phosphate buffer or polyalcohol solutions, e.g. mannitol solutions, can also be used for the hydration of the film.

EXAMPLE 10

A mixed micelle solution of vitamin A palmitate having the following composition was prepared as described below:

| | |
|---|---|
| Vitamin A palmitate | 5000 IU |
| Glycocholic acid | 23.6 mg |
| Lecithin | 35.0 mg |
| Propylene glycol | 50.0 mg |
| Ethanol | 50.0 mg |
| NaOH ad pH 6.0 | q.s. mg |
| Benzyl alcohol | 10.0 mg |
| Water ad | 1000.0 mg |

The glycocholic acid, lecithin and vitamin A palmitate stabilized with tocopherol were dissolved in a mixture of propylene glycol, ethanol and benzyl alcohol to give a clear solution. The pH value of the solution was adjusted to 6.0±0.1 with NaOH.

EXAMPLE 11

Tocopherol acetate mixed micelle solutions for topical use having following compositions were prepared as described below:

| 11a) Formulations with Na glycocholate as the detergent: | | |
|---|---|---|
| | a1 | a2 |
| dl-$\alpha$-Tocopherol acetate | 2.0 | 5.0 g |

| 11a) Formulations with Na glycocholate as the detergent: | | |
| --- | --- | --- |
| | a1 | a2 |
| dl-α-Tocopherol | 0.05 | 0.05 g |
| Na glycocholate | 2.0–3.39 | 5.0 g |
| Lecithin | 3.0–5.0 | 10.0 g |
| Propylene glycol | 5.0 | 5.0 g |
| Ethanol | 5.0 | 5.0 g |
| Benzyl alcohol | 1.0 | 1.0 g |
| Water ad | 100.0 | 100.0 g |

The solutions were prepared by adding the ethanol. tocopherol, tocopherol acetate, propylene glycol, benzyl alcohol, lecithin and Na glycocholate in succession and dissolved with slight warming to give a clear solution. Thereafter, the solution was treated with water and the pH value was adjusted to 6.0.

Formulations of tocopherol acetate (2%) based on lecithin-cholanic acid salt-mixed micelles were distinguishable from conventional tocopherol acetate solubilizates in that only physiological solubilizers were used. Moreover, the in vitro skin penetration from the mixed micelle solution was somewhat better than from an analogous conventional solubilizate using 10% PEG-36 castor oil.

After a penetration period of 6 h, the following distribution in the hog skin was determined:

TABLE IV

| Formulation with 2% tocopherol acetate | Skin surface | Str. corneum | Remaining skin |
| --- | --- | --- | --- |
| Mixed micelle solution* | 88.8% | 8.9% | 2.3% |
| Conventional solubilizate | 90.4% | 7.8% | 1.8% |

*3.5% lecithin and 2.47% Na glycocholate

| 11b Formulations with Na cholate as the detergent: | |
| --- | --- |
| dl-α-Tocopherol acetate | 2.0 g |
| dl-α-Tocopherol | 0.05 g |
| Na cholate | 2.5 g |
| Lecithin | 3.0 g |
| Propylene glycol | 5.0 g |
| Ethanol | 5.0 g |
| Water ad | 100.0 g |

A solution of tocopherol acetate and tocopherol (2.0+0.05 g) in ethanol, and lecithin (3.0 g) dissolved in chloroform/methanol (1:1), were mixed and dried in a vacuum to a film. The film was dissolved in 5.0 g of ethanol and 5.0 g of warm propylene glycol. Subsequently, this solution was treated with an aqueous solution of 2.0 g of Na cholate, shaken and warmed. The pH value was adjusted to 6.0±0.1 with 1N HCl and the solution was made up to 100 g with water. The resulting solution was then stirred at RT until a clear solution was obtained (about 18 h.).

Many modifications and variations of this invention may be made without departing from its spirit and scope, as will become apparent to those skilled in the art. The specific embodiments described herein are offered by way of example only, and the invention is to be limited only by the terms of the appended claims.

We claim:

1. A method of facilitating penetration and distribution of a pharmaceutically active substance into the skin of a host, comprising applying a mixed micelle preparation to the skin, which preparation includes said pharmaceutically active substance, a salt of a cholanic acid, and phosphatidylcholine in an amount effective to facilitate penetration and distribution of said substance into the skin.

2. The method of claim 1, wherein sodium glycocholate is the salt of the cholanic acid.

3. The method of claim 1, in which the active substance is selected from the group consisting of a retinoid, an antimycotic and panthenol.

4. The method of claim 1, wherein sodium glycocholate is the salt of the cholanic acid and the phosphatidylcholine is lecithin.

5. The method of claim 1, which is the form of a solution or a gel.

* * * * *